United States Patent [19]
Brown et al.

[11] Patent Number: 5,135,617
[45] Date of Patent: Aug. 4, 1992

[54] SEPARATION OF AROMATIC FROM OLEFINIC HYDROCARBONS BY EXTRACTIVE DISTILLATION

[75] Inventors: Ronald E. Brown; Michael S. Matson, both of Bartlesville, Okla.

[73] Assignee: Phillips Petroleum Company, Bartlesville, Okla.

[21] Appl. No.: 724,050

[22] Filed: Jul. 1, 1991

[51] Int. Cl.$^5$ .............................................. B01D 3/40
[52] U.S. Cl. ........................................ 203/56; 203/58; 203/63; 585/808; 585/860; 585/865
[58] Field of Search ................. 203/51, 56, 58, 63; 585/810, 804, 833, 860, 865, 807, 808

[56] References Cited

U.S. PATENT DOCUMENTS

| | | | |
|---|---|---|---|
| 2,508,723 | 5/1950 | Mayland et al. | 585/866 |
| 2,736,755 | 2/1956 | Reuter et al. | 55/84 |
| 2,891,894 | 6/1959 | Cier et al. | 203/60 |
| 3,157,592 | 11/1964 | Fuerst | 208/324 |
| 3,591,490 | 7/1971 | Müller et al. | 208/313 |
| 3,723,256 | 3/1973 | Thompson | 203/43 |
| 3,803,258 | 4/1974 | Weitz et al. | 585/862 |
| 4,053,369 | 10/1977 | Cines | 203/52 |
| 4,278,505 | 7/1981 | Danulat et al. | 203/59 |
| 4,421,640 | 12/1983 | Watson et al. | 208/326 |
| 4,921,581 | 5/1990 | Lee et al. | 203/56 |
| 4,944,849 | 7/1990 | Lee | 203/55 |
| 4,948,470 | 8/1990 | Lee | 203/51 |
| 4,948,472 | 8/1990 | Lee et al. | 203/55 |
| 4,954,224 | 9/1990 | Brown et al. | 203/51 |
| 4,955,468 | 9/1990 | Lee | 203/53 |
| 5,032,232 | 7/1991 | Lee et al. | 203/51 |

Primary Examiner—Virginia Manoharan
Attorney, Agent, or Firm—K. K. Brandes

[57] ABSTRACT

Aromatic hydrocarbons containing 6–10 carbon atoms per molecule are separated from close-boiling olefinic hydrocarbons by extractive distillation employing N-(β-hydroxyethyl)-2-pyrrolidone and/or cyclohexanol as solvent.

19 Claims, 1 Drawing Sheet

SEPARATION OF AROMATIC FROM OLEFINIC HYDROCARBONS BY EXTRACTIVE DISTILLATION

BACKGROUND OF THE INVENTION

This invention relates to the separation of aromatic hydrocarbons from close-boiling mono- and/or diolefins by extractive distillation.

Extractive distillation is a well known technique for separating mixtures of components having a relative volatility close to unity (i.e., having nearly equal volatility and having nearly the same boiling point). It is difficult to separate the components of such mixtures by conventional fractional distillation. In extractive distillation, a solvent is introduced into a distillation column above the entry point of the feed mixture which is to be separated. The solvent affects the volatility of the higher boiling feed component(s) sufficiently to facilitate the separation of the various feed components by distillation and exits with the bottoms fraction, as has been described in the article entitled "Extractive Distillation Saves Energy" by Ian Sucksmith, Chemical Engineering, Jun. 28, 1982, pages 91-95. Other literature sources on extractive distillation techniques include the "Handbook of Separation Techniques for Chemical Engineers" by Philip A. Schweitzer, McGraw-Hill Book Company, 1979, pages 1-135 to 1-143; and Perry's Chemical Engineers Handbook, 6th Edition, McGraw-Hill Book Company 1984, pages 13-53 to 13-57.

SUMMARY OF THE INVENTION

It is an object of this invention to provide a process for separating aromatic hydrocarbons from close-boiling olefinic hydrocarbons by extractive distillation employing a selective solvent (also referred to as extractant or entrainer). Other objects and advantages will be apparent from the detailed description of the invention and the appended claims.

In accordance with this invention, a process for separating at least one aromatic hydrocarbon containing 6-10 carbon atoms per molecule from at least one close-boiling olefinic hydrocarbon selected from the group consisting of alkenes, alkadienes, cycloalkenes, cycloalkadienes and mixtures thereof (i.e., mixtures of any two or more than two olefinic hydrocarbons) by extractive distillation of a feed comprising (preferably consisting essentially of) said at least one aromatic hydrocarbon and said at least one close-boiling olefinic hydrocarbon employs a solvent comprising (preferably consisting essentially of) at least one hydroxy-compound selected from the group consisting of N-($\beta$-hydroxyethyl)-pyrrolidone, cyclohexanol and mixtures thereof.

DETAILED DESCRIPTION OF THE INVENTION

Figure 1:
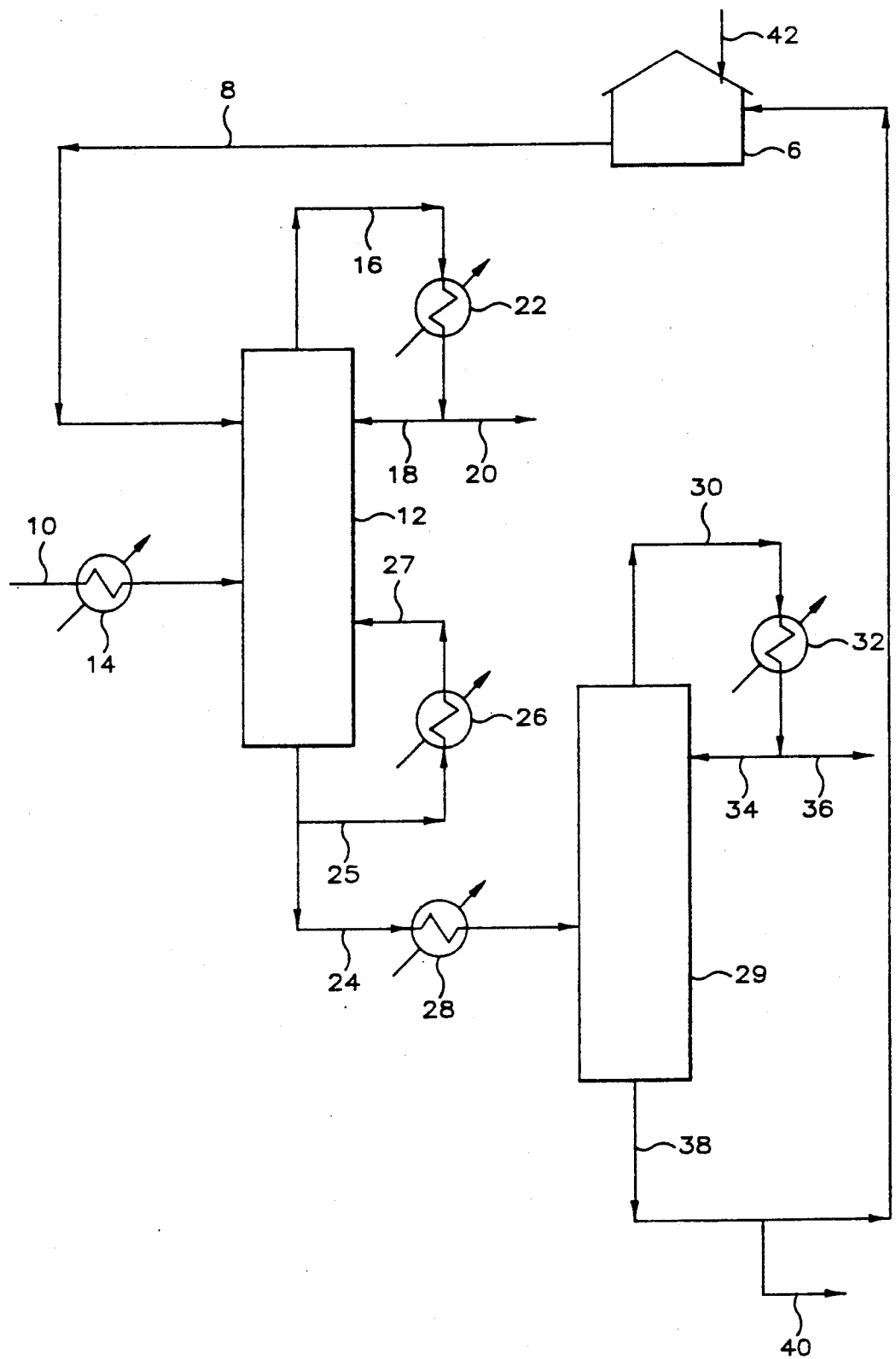
FIG. 1 illustrates the extractive distillation process of this invention.

In an extractive distillation process, an agent (called "solvent" or "extractant" or "entrainer") is added to a feed mixture of components to be separated so that the relative volatilities of the components of the mixture are changed such that a sufficient difference in volatility of the components results and effective separation by distillation becomes possible. The added solvent is usually chosen so as to exhibit high "selectivity" regarding the components to be separated. Selectivity is a term related to the change in volatilities of components in the mixture caused by the presence of the solvent. The larger the difference in relative volatility of the components in the mixture, the easier the separation of the components by fractional distillation becomes. Therefore, a solvent of high selectivity is a solvent which causes great differences between the relative volatilities of the components in a mixture, and will allow for the separation of components in a mixture with fewer distillation stages, lower amount of reflux and higher product purity. The term "close-boiling" as used herein, means that the aromatic hydrocarbon(s) and the olefinic hydrocarbon(s) contained in the feed have nearly the same boiling point at atmospheric pressure.

In the process of this invention, any hydrocarbon feed which contains at least one aromatic hydrocarbon containing 6-10 carbon atoms per molecule and at least one close-boiling olefinic hydrocarbon (preferably containing 5-10 carbon atoms per molecule) can be used in the extractive distillation process of this invention. Preferably, the boiling points (at atmospheric pressure conditions, i.e., at about 1 atm.) of the aromatic hydrocarbon(s) and of the olefinic hydrocarbon(s) to be separated by extractive distillation process of this invention, are in the range of from about 150° to about 500° F., more preferably about 170°-400° F. Generally, the boiling points of the aromatic and olefinic hydrocarbons differ by about 0.2°-10° F. (preferably about 0.5°-5° F.), at about 1 atm.

Preferably, the aromatic hydrocarbon content in the feed is about 5-95 weight-% (more preferably about 20-80 weight-%), and the olefinic hydrocarbon content is about 5-95 weight-% (more preferably about 20-80 weight-%). When more than one type of olefinic hydrocarbon is present in the feed, e.g., alkene(s) and cycloalkene(s), or alkene(s) and alkadiene(s), or alkadiene(s) and cycloalkene(s), or alkene(s), alkadiene(s) and cycloalkadiene(s), etc., the various types of olefinic hydrocarbons can be present at any weight ratio.

Non-limiting examples of suitable aromatic hydrocarbons are benzene, toluene, meta-xylene, ortho-xylene, para-xylene, ethylbenzene, trimethylbenzenes, methylethylbenzenes, and the like, and mixtures of the above. Preferred aromatic hydrocarbons are benzene, toluene and the xylenes.

Non-limiting examples of suitable alkenes (aliphatic monoolefins) are 1-pentene, 2-pentene, 2-methyl-1-butene, 1-hexene, 2-hexene, 3-hexene, 2-methyl-1-pentene, 2-methyl-2-pentene, 3-methyl-1-pentene, 2,3-dimethyl-1-butene, 1-heptene, 2-heptene, 3-heptene, 2-methyl-1-hexene, 2-methyl-2-hexene, 3-methyl-2-hexene, 3-methyl-3-hexene, 3,3-dimethyl-1-pentene, 1-octene, 2-octene, 3-octene, 2-methyl-1-heptene, 1-nonene, 2-nonene, 3-nonene, 1-decene, 2-decene, and mixtures thereof; preferably 1-nonene.

Non-limiting examples of suitable alkadienes (aliphatic diolefins) include 1,2-butadiene, 1,3 butadiene, isoprene, 1,2-pentadiene, 1,3-pentadiene, 2,4-pentadiene, 1,2-hexadiene, 1,3-hexadiene, 1,5-hexadiene, 2,4-hexadiene, 2-methyl-1,2-pentadiene, 2-methyl-1,3-pentadiene, 1,2-heptadiene, 1,3-heptadiene, 2,4-heptadiene, 2-methyl-1,2-hexadiene, 3-methyl-1,2-hexadiene, 2-methyl-1,3-hexadiene, 3-methyl-1,3-hexadiene, 1,2-octadiene, 1,3-octadiene, 2,4-octadiene, 1,5-octadiene, 2-methyl-1,2-heptadiene, 3-methyl-1,2-heptadiene, 2- methyl-1,3-heptadiene, 3-methyl-1,3-heptadiene, 3-ethyl-1,2-pentadiene, 3-ethyl-1,3-pentadiene, 1,2-nonadiene, 1,3-nonadiene, 2,4-nonadiene, 2-methyl-1,2-octadiene, 3-methyl-1,2-octadiene, 3-methyl-1,3-octadiene, 3-ethyl-1,3-heptadiene, 3-ethyl-2,4-heptadiene, and mixtures thereof; preferably 1,5-hexadiene.

Non-limiting examples of suitable cycloalkenes (cyclomonoolefins) include cyclopentene, cyclohexene, 1-methylcyclopentene, 2-methylcyclopentene, 3-methylcyclopentene, cycloheptene, 1-methylcyclohexane, 2-methylcyclohexene, 3-methylcyclohexene, 3-ethylcyclopentene, 1,2-dimethylcyclopentene, 2,3-dimethylcyclopentene, cyclooctene, 1-methylcycloheptene, 2-methylcyclopentene, 3-methylcyclopentene, 1-ethylcyclohexene, 2-ethylcyclohexene, 3-ethylcyclohexene, 1,2-dimethylcyclohexene, 1,3-dimethylcyclohexene, 2,3-dimethylcyclohexene, 1-methylcyclooctene, 2-methylcyclooctene, 3-methylcyclooctene, 4-methylcyclooctene, 1-ethylcyclooctene, 2-ethylcyclooctene, 3-ethylcyclooctene, 4-ethylcyclooctene, 1,2-dimethyl-cyclooctene, 1,3-dimethylcyclooctene, 2,3-dimethylcyclooctene, 2,4-dimethyloctene, and mixtures thereof; preferably cyclohexene.

Non-limiting examples of suitable cycloalkadienes (cyclodiolefins) include 1,2-cyclopentadiene, 1,3-cyclopentadiene, 1,3-cyclohexadiene, 1-methyl-1,2-cyclopentadiene, 2-methyl-1,2-cyclopentadiene, 3-methyl-1,2-cyclopentadiene, 1-methyl-1,3-cyclopentadiene, 2-methyl-1,3-cyclopentadiene, 3-methyl-1,3-cyclopentadiene, 1,2-cycloheptadiene, 1,3-cycloheptadiene, 1,4-cycloheptadiene, 1-methyl-1,2-cyclohexadiene, 1-methyl-1,3-cyclohexadiene, 2-methyl-1,2-cyclohexadiene, 2-methyl-1,3-cyclohexadiene, 1-ethyl-1,2-cyclopentadiene, 1-ethyl-1,3-cyclopentadiene, 2-ethyl-1,3-cyclopentadiene, 3-ethyl-1,3-cyclopentadiene, 1,2-dimethyl-1,2-cyclopentadiene, 1,2-dimethyl-1,3-cyclopentadiene, 1,3-dimethyl-1,3-cyclopentadiene, 1,3-dimethyl-1,3-cyclohexadiene, 1,3-dimethyl-1,3-cyclohexadiene, 1,2,3-trimethyl-1,3-cyclohexatriene, and mixtures thereof.

Cyclohexanol, one of the solvents employed in the process of this invention, is well known and is commercially available. The other solvent, N-(β-hydroxyethyl)-2-pyrrolidone having the structural formula

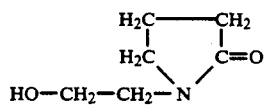

can be prepared by the non-catalytic reaction of ethanolamine ($H_2N-CH_2-CH_2-OH$) and butyrolactone (a cyclic ester having the general formula $C_4H_6O_2$) at an elevated temperature, preferably at about 200°–400° C. Preferably, the reaction is carried out in an autoclave with stirring under autogenous pressure. The formed product, N-(β-hydroxyethyl)-2-pyrrolidone (boiling point: 320° C. at 1 atm; 145° C. at 1 mm Hg) can be separated from the remainder of the reaction mixture by fractional distillation.

Any suitable weight ratio of the solvent to the hydrocarbon containing feed mixture can be employed. Generally, the solvent to feed weight ratio is in the range of from about 1:1 to about 40:1, preferably in the range of from about 5:1 to about 20:1. Preferably, either N-(β-hydroxyethyl)-2-pyrrolidone alone or cyclohexanol alone is employed as a solvent. But it is within the scope of this invention to employ a mixture of these two compounds at any suitable weight ratio (generally at a weight ratio of 1:20 to about 20:1) as a solvent.

Any suitable reflux ratio (i.e., the weight ratio of the portion of condensed vapor which is returned to the distillation column to the portion of condensed vapor which is withdrawn as distillate product) can be employed in the extractive distillation process of this invention. Generally the reflux ratio is in the range of from about 0.1:1 to about 100:1, preferably in the range of from about 0.5:1 to about 50:1, more preferably in the range of from about 1:1 to about 20:1.

Any suitable feed entry location can be selected. Generally the feed entry location is in the range of from about 2 to about 70 percent of the total height of the packed or trayed column, measured upward from the bottom of the column, preferably in the range of from about 5 to about 60 percent, more preferably in the range of from about 7 to about 70 percent.

Any suitable solvent entry location can be selected. Generally the solvent entry location is in the range of from about 50 to about 99 percent of the total height of the packed or trayed column (i.e., within the upper half of the column), preferably in the range of from about 70 to about 99 percent, more preferably in the range of from about 80 to about 99 percent.

Any suitable temperature in the reboiler vessel (containing primarily the higher boiling feed components and the solvent) can be employed. The temperature is generally in the range of from about 200° to about 500° F., preferably in the range of from about 250° to about 450° F. The extractive distillation column is generally heated (more near the bottom, and less near the top). Generally, the temperature at the top of the column where the vapor exits into the condenser is in the range of from about 80° to about 350° F., preferably in the range of from about 100° to about 250° F. Solvent and feed are generally preheated (generally to a temperature close to the column temperature of the corresponding entry point) before they are introduced into the column. Any suitable pressure can be employed during the extractive distillation. Generally the pressure is about 5 to about 100 psig, preferably about 8 to about 20 psig.

The overhead distillate product (withdrawn from the top of the column) generally contains a smaller volume percentage of the aromatic hydrocarbon(s) than the feed and a larger volume percentage of the olefinic hydrocarbon(s) than the feed. The bottoms product (a portion of which can be reheated and recycled to the lower portion of the column) contains a larger volume percentage of the aromatic hydrocarbon(s) than the feed and a smaller volume percentage of the olefinic hydrocarbon(s) than the feed. Furthermore, the bottoms product contains essentially all of the added solvent, which can be separated from the other bottoms product components by distillation or other suitable separating means and then be recycled to the extractive distillation column.

Any suitable total column height, packed column height, column diameter and number of trays in the extraction distillation column can be employed. The exact dimensions and column designs depend on the scale of the operation, the exact feed composition, the exact solvent composition, the desired recovery and degree of purity of the various product, and the like, and can be determined by those having ordinary skills in the art.

The invention can be better understood by reference to FIG. 1 and the following description of a preferred embodiment of the invention. The feed mixture comprising aromatic hydrocarbon(s) and close-boiling olefinic hydrocarbon(s) is introduced through conduit 10 to a fractionation zone such as multi-stage distillation column 12. The temperature of the feed mixture flowing through conduit 10 can be adjusted as needed by controlling heat exchanger 14 so as to add heat to or remove heat from the feed mixture. Solvent from solvent storage 6 is introduced to distillation column 12 through conduit 8, and an overhead stream enriched in olefinic hydrocarbon(s) is withdrawn from an upper portion of distillation column 12 through conduit 16. This overhead stream can be completely passed to storage or to other processing units or, as is often the case, the overhead stream can be partially or totally condensed, with a portion thereof being returned to the fractionation zone as reflux. The overhead stream passing through conduit 16 is condensed in condenser 22 to yield a condensed overhead stream. A portion of the condensed overhead stream can be returned to distillation column 12 as reflux through conduit 18, while the remainder of the condensed overhead stream is yielded as product or passed to other processing units through conduit 20.

A bottoms stream is withdrawn from a lower portion of the fractionation zone represented by distillation column 12 through conduit 24. A portion of the fluids withdrawn from the bottom of distillation column 12 may be heated and returned to distillation column 12. For example, a portion of the bottoms product stream can be withdrawn through conduit 25, heated in reboiler 26 and then passed back to a lower portion of distillation column 12 through conduit 27.

Operating conditions in heat exchanger 14, condenser 22 and reboiler 26 can be controlled and interfaced with solvent flow through conduit 8, feed mixture flow through conduit 10, reflux flow through conduit 18 and bottoms stream flow through conduit 24 such that the feed mixture introduced into distillation column 12 will be fractionated to yield an overhead stream which is enriched in olefinic hydrocarbon(s) and a bottoms stream predominantly comprising the aromatic hydrocarbon(s) and the solvent.

The bottoms stream passing through conduit 24 can be passed to storage, used in other processes or, preferably, passed to another fractionation zone, such as distillation column 29. Any adjustments to the temperature of the bottoms stream passing through conduit 24 necessary for efficient fractionation in distillation column 29 can be made by appropriately adjusting heat exchanger 28. An overhead stream predominantly comprising aromatic hydrocarbon(s) is withdrawn from an upper portion of distillation column 29 through conduit 30. This overhead stream can be at least partially condensed in condenser 32. A portion of the overhead stream withdrawn from condenser 32 can be returned through conduit 34 as reflux for distillation column 29, with the remainder of the overhead stream being withdrawn as product, i.e., aromatic hydrocarbon(s) of high purity (preferably higher than 95%), through conduit 36.

A bottoms stream predominantly comprising the solvent is withdrawn from a lower portion of distillation column 29 through conduit 38. A portion of this bottoms stream is preferably routed back to solvent storage 6 and then recycled to distillation column 12, while another portion of the bottoms stream is heated in a reboiler (not shown) and returned to the lower portion of column 29. From time to time, impurities which may build up in the solvent can be removed from the system by removing a small purge stream through conduit 40. Solvent lost through the purge stream or through other processing losses may be made up by a makeup stream passing through conduit 42 and into solvent storage 6.

The following examples are presented to further illustrate the invention and are not to be considered unduly limiting the scope of this invention.

EXAMPLE I

This example demonstrates the superiority as solvent of N-($\beta$-hydroxyethyl)-N-pyrrolidone (HEP) over N-methyl-2-pyrrolidone (NMP) in the extractive distillation of a feed of an aromatic hydrocarbon and a cycloalkene.

To a hydrocarbon mixture of 50 weight-% benzene and 50 weight-% cyclohexene was added an extractive solvent (either HEP or NMP) at various solvent:feed weight ratios. The total mixture (including the extractive solvent) was heated under reflux conditions for about 20-30 minutes in a distillation flask equipped with a reflux condenser. Then a small sample was withdrawn by means of a septum from the flask containing the liquid phase of the equilibrium system, and a sample of the condensed vapor was withdrawn by means of a septum located just below the reflux condenser. Both samples were analyzed, and the mole fractions of benzene and cyclohexene in the liquid phase and in the vapor phase were determined by means of a gas chromatograph. The relative volatility R was calculated as follows:

$$R = \frac{Y1/Y2}{X1/X2} = \frac{Y1/X1}{Y2/X2},$$

wherein Y1 and Y2 are the mole fractions of cyclohexene and benzene, respectively, in the vapor phase; and X1 and X2 are the mole fractions of cyclohexene and benzene, respectively, in the liquid phase. Test results are summarized in Table I.

TABLE I

| Solvent:Feed Weight Ratio | Added Solvent | Relative Volatility R |
|---|---|---|
| 3:1 | HEP | 1.73 |
| 3:1 | NMP | 1.59 |
| 5:1 | HEP | 1.90 |
| 5:1 | NMP | 1.62 |
| 7:1 | HEP | 2.07 |
| 7:1 | NMP | 1.63 |

Based on the test results in Table I, it is concluded that N-($\beta$-hydroxyethyl)-2-pyrrolidone will be more effective than N-methyl-2-pyrrolidone as solvent in the extractive distillation of feeds containing aromatic hydrocarbon(s) and close-boiling cycloalkene(s), in particular at commercially most feasible solvent:feed weight ratios of about 3:1 and higher.

EXAMPLE II

This example demonstrates the superiority as solvent of HEP over NMP in the extractive distillation of an aromatic hydrocarbon and an alkadiene.

Tests were carried out substantially in accordance with the procedure described in Example I, except that a feed mixture of 50 weight-% benzene and 50 weight-% 1,5-hexadiene was used. Liquid and vapor samples were analyzed and the mole fractions of benzene and 1,5-hexadiene in the liquid phase and in the vapor phase were determined by means of a gas chromatograph. The relative volatility $R^1$ was calculated as follows:

$$R^1 = \frac{Y3/Y4}{X3/X4} = \frac{Y3/X3}{Y4/X4},$$

wherein Y3 and Y4 are the mole fractions of 1,5-hexadiene and benzene, respectively, in the vapor phase; and X3 and X4 are the mole fractions of 1,5 hexadiene and benzene, respectively, in the liquid phase. Test results are summarized in Table II.

TABLE II

| Solvent:Feed Weight Ratio | Added Solvent | Relative Volatility $R^1$ |
| --- | --- | --- |
| 3:1 | HEP | 3.44 |
| 3:1 | NMP | 3.05 |
| 5:1 | HEP | 3.77 |
| 5:1 | NMP | 3.04 |
| 7:1 | HEP | 4.2 |
| 7:1 | NMP | 2.84 |

Based on test results in Table II, it is concluded that N-(β-hydroxyethyl)-2-pyrrolidone will be more effective than N-methyl-2pyrrolidone as solvent in the extractive distillation of feeds of aromatic hydrocarbon(s) and close-boiling alkadiene(s), especially at a solvent:feed ratio of about 3:1 and higher.

EXAMPLE III

This example demonstrates the utility of cyclohexanol as solvent in the extractive distillation of an aromatic hydrocarbon and an alkene.

Tests were carried out substantially in accordance with the procedure described in Example I, except that a feed of 50 weight-% o-xylene and 50 weight-% 1-nonene was used. Liquid and vapor samples were analyzed and the mole fractions of o-xylene and 1-nonene in the liquid phase and in the vapor phase were determined by means of a gas chromatograph. The relative volatility $R^2$ was calculated as follows:

$$R^2 = \frac{Y5/Y6}{X5/X6} = \frac{Y5/X5}{Y6/X6},$$

wherein Y5 and Y6 are the mole fractions of 1-nonene and o-xylene, respectively, in the vapor phase; and X5 and X6 are the mole fractions of 1-nonene and o-xylene, respectively, in the liquid phase. Test results are summarized in Table III.

TABLE III

| Solvent:Feed Weight Ratio | Added Solvent | Relative Volatility $R^2$ |
| --- | --- | --- |
| 1:1 | Cyclohexanol | 1.89 |
| 3:1 | Cyclohexanol | 2.88 |
| 5:1 | Cyclohexanol | 3.80 |
| 7:1 | Cyclohexanol | 4.48 |

Based on test results in Table III, it is concluded that cyclohexanol will be effective as a solvent in the extractive distillation of feeds of aromatic hydrocarbon(s) and close-boiling olefinic hydrocarbon(s), in particular at commercially most feasible solvent:feed weight ratios of about 5:1 and higher. Additional tests (not herein described in detail) indicated that cyclohexanol was considerably more effective as solvent in the extractive distillation of the above-described feed than N-methyl-2-pyrrolidone and sulfolane, respectively.

Reasonable variations, modifications and adaptations for various usages and conditions can be made within the scope of the disclosure and the appended claims, without departing from the scope of this invention.

That which is claimed is:

1. A process for separating at least one aromatic hydrocarbon containing 6–10 carbon atoms per molecule from at least one olefinic hydrocarbon containing 5–10 carbon atoms per molecule selected from the group consisting of alkenes, alkadienes, cycloalkenes and cycloalkadienes which consists essentially of extractive distillation of a feed consisting essentially of said at least one aromatic hydrocarbon and said at least one olefinic hydrocarbon employing a solvent consisting essentially of N-(β-hydroxyethyl)-2-pyrrolidone;

wherein said process produces (i) an overhead product which contains a smaller volume percentage of said at least one aromatic hydrocarbon and a larger volume percentage of said at least one olefinic hydrocarbon than said feed, and (ii) a bottoms product which contains said solvent and a larger volume percentage of said at least one aromatic hydrocarbon and a smaller volume percentage of said at least one olefinic hydrocarbon than said feed.

2. A process in accordance with claim 1, wherein said at least one aromatic hydrocarbon is selected from the group consisting of benzene, toluene and xylenes.

3. A process in accordance with claim 1, wherein said at least one olefinic hydrocarbon is selected from the group consisting of 1-nonene, 1,5-hexadiene and cyclohexene.

4. A process in accordance with claim 1, wherein said feed boils at a temperature in the range of about 150° F. to about 500° F., at atmospheric pressure conditions.

5. A process in accordance with claim 1, wherein the weight ratio of said solvent to said feed is in the range of about 1:1 to about 40:1.

6. A process in accordance with claim 1, further consisting essentially of the step of separating said at least one aromatic hydrocarbon from said solvent contained in said bottoms product.

7. A process for separating at least one aromatic hydrocarbon containing 6–10 carbon atoms per molecule from at least one olefinic hydrocarbon containing 5–10 carbon atoms per molecule selected from the group consisting of alkenes, alkadienes, cycloalkenes and cycloalkadienes which consists essentially of extractive distillation of a feed consisting essentially of said at least one aromatic hydrocarbon and said at least one olefinic hydrocarbon employing a solvent consisting essentially of cyclohexanol;

wherein said process produces (i) an overhead product which contains a smaller volume percentage of said at least one aromatic hydrocarbon and a larger volume percentage of said at least one olefinic hydrocarbon than said feed, and (ii) a bottoms product which contains said solvent and a larger volume percentage of said at least one aromatic hydrocarbon and a smaller volume percentage of said at least one olefinic hydrocarbon than said feed.

8. A process in accordance with claim 7, wherein said at least one aromatic hydrocarbon is selected from the group consisting of benzene, toluene and xylenes.

9. A process in accordance with claim 7, wherein said at least one olefinic hydrocarbon is selected from the group consisting of 1-nonene, 1,5-hexadiene and cyclohexene.

10. A process in accordance with claim 7, wherein said feed boils at a temperature in the range of about 150° F. to about 500° F., at atmospheric pressure conditions.

11. A process in accordance with claim 7, wherein the weight ratio of said solvent to said feed in the range of about 1:1 to about 40:1.

12. A process in accordance with claim 7, further consisting essentially of the step of separating said at least one aromatic hydrocarbon from said solvent contained in said bottoms product.

13. A process for separating at least one aromatic hydrocarbon containing 6-10 carbon atoms per molecule from at least one olefinic hydrocarbon containing 5-10 carbon atoms per molecule selected from the group consisting of alkenes, alkadienes, cycloalkenes and cycloalkadienes which consists essentially of extractive distillation of a feed consisting essentially of said at least one aromatic hydrocarbon and said at least one olefinic hydrocarbon employing a solvent consisting essentially of a mixture of N-($\beta$-hydroxyethyl)-2-pyrrolidone and cyclohexanol;

wherein said process produces (i) an overhead product which contains a smaller volume percentage of said at least one aromatic hydrocarbon and a larger volume percentage of said at least one olefinic hydrocarbon than said feed, and (ii) a bottoms product which contains said solvent and a larger volume percentage of said at least one aromatic hydrocarbon and a smaller volume percentage of said at least one olefinic hydrocarbon than said feed.

14. A process in accordance with claim 13, wherein said at least one aromatic hydrocarbon is selected from the group consisting of benzene, toluene and xylenes.

15. A process in accordance with claim 13, wherein said at least one olefinic hydrocarbon is selected from the group consisting of 1-nonene, 1,5-hexadiene and cyclohexene.

16. A process in accordance with claim 13, wherein said feed boils at a temperature in the range of about 150° F. to about 500° F., at atmospheric pressure conditions.

17. A process in accordance with claim 13, wherein the weight ratio of N-($\beta$-hydroxyethyl)-2-pyrrolidone to cyclohexanol in said solvent is in the range of about 1:20 to about 20:1.

18. A process in accordance with claim 13, wherein the weight ratio of said solvent to said feed is in the range of about 1:1 to about 40:1.

19. A process in accordance with claim 13, further consisting essentially of the step of separating said at least one aromatic hydrocarbon from said solvent contained in said bottoms product.

* * * * *